US 6,590,402 B2

(12) United States Patent
Wang et al.

(10) Patent No.: US 6,590,402 B2
(45) Date of Patent: *Jul. 8, 2003

(54) ENGINE OIL CONTAMINATION SENSOR

(75) Inventors: Su-Chee Simon Wang, Troy, MI (US); Yingjie Lin, El Paso, TX (US)

(73) Assignee: Delphi Technologies, Inc., Troy, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/969,222

(22) Filed: Oct. 2, 2001

(65) Prior Publication Data

US 2003/0062910 A1 Apr. 3, 2003

(51) Int. Cl.[7] .................. G01R 27/08; G01R 27/26; G08B 19/00; G08B 13/26
(52) U.S. Cl. .................. 324/698; 324/663; 340/522; 340/603; 340/604; 340/631; 340/668
(58) Field of Search ............... 324/698, 663, 324/441, 668; 73/53.05; 701/30; 123/196.5; 340/522, 603, 604, 631

(56) References Cited

U.S. PATENT DOCUMENTS

| 2,004,569 A | * | 6/1935 | Davis, Jr. ............... 324/444 |
| 3,331,019 A | * | 7/1967 | Irwin ..................... 324/686 |
| 4,007,629 A | * | 2/1977 | Hochstein .............. 73/53.04 |
| 4,506,337 A | * | 3/1985 | Yasuhara ................ 701/30 |
| 4,686,857 A | * | 8/1987 | Kato ..................... 324/698 |
| 4,694,793 A | * | 9/1987 | Kawakita et al. ...... 123/196 S |
| 4,733,556 A | * | 3/1988 | Meitzler et al. ........ 73/53.05 |
| 4,862,393 A | * | 8/1989 | Reid et al. .............. 701/30 |
| 4,970,492 A | * | 11/1990 | King ................... 340/450.3 |
| 5,274,335 A | * | 12/1993 | Wang et al. ............ 324/689 |
| 5,789,665 A | * | 8/1998 | Voelker et al. ......... 73/53.05 |
| 6,253,601 B1 | * | 7/2001 | Wang et al. ............ 73/117.3 |
| 6,278,281 B1 | * | 8/2001 | Bauer et al. ............ 324/441 |
| 6,380,746 B1 | * | 4/2002 | Polczynski et al. ..... 324/446 |
| 6,443,006 B1 | * | 9/2002 | Degrave ................ 73/304 |

OTHER PUBLICATIONS

Basu et al., "Smart Sensing" of oil degradation and oil level measurements in gasoline engines, SAE Technical paper series (2000–01–1366), SAE International.*

* cited by examiner

Primary Examiner—Christine Oda
Assistant Examiner—Wassem H. Hamdan
(74) Attorney, Agent, or Firm—Margaret A. Dobrowitsky

(57) ABSTRACT

An engine oil contamination sensor includes a first sensing electrode and a second sensing electrode. A sensing area is established between the electrodes. The sensor is oriented in an oil pan such that the sensing area is completely submerged in engine oil. A microprocessor is connected to the sensing electrodes and includes a program for determining whether antifreeze is dispersed in the engine oil.

16 Claims, 2 Drawing Sheets

ENGINE OIL CONTAMINATION SENSOR

TECHNICAL FIELD

The present invention relates generally to oil condition sensors.

BACKGROUND OF THE INVENTION

A major threat to vehicle engine oil is antifreeze leaking into the oil system from the coolant system. Antifreeze in concentrations as low as a few hundred parts-per-million (ppm) can cause detrimental changes in the engine oil. For example, sludge deposits can form at the location where the antifreeze leaks into the oil. Moreover, the antifreeze in the oil can react with anti-wear additives, e.g., zinc alkyldithiophosphate (ZDP). If a significant amount of ZDP is affected, anti-wear protection may be lost, and catastrophic camshaft and valve lifter wear will result. Also, the loss of the ZDP could hasten the degradation of the engine oil.

Under normal operating conditions, small amounts of antifreeze leaking into the engine oil is dispersed by dispersants and detergents in the engine oil. After dispersal, the adverse effects of antifreeze on the engine components and engine oil would be reduced considerably. However, continuous antifreeze leakage would eventually deplete all of the dispersants, and any undispersed antifreeze can cause the problems mentioned above.

Current sensors exist which detect undispersed antifreeze in engine oil. Since undispersed antifreeze does not mix with the engine oil, but rather settles at the bottom of the oil pan, it can be detected by an engine oil condition sensor located at the bottom of the pan. These sensors, however, do not detect dispersed antifreeze. Consequently, until all of the dispersants are depleted and undispersed antifreeze begins to collect in the bottom of the oil pan, the driver is unaware of an antifreeze leak into the engine oil and is unable to have the leak repaired before damage to the engine occurs.

The present invention has recognized these prior art drawbacks, and has provided the below-disclosed solutions to one or more of the prior art deficiencies.

SUMMARY OF THE INVENTION

A method for determining dispersed antifreeze contamination of oil within an engine using an oil contamination sensor includes starting the engine and heating the oil. The output voltage of the sensor is measured and based on the output voltage of the sensor, it is determined whether antifreeze is being dispersed in the oil.

In one aspect of the present invention, the oil has a relatively rapid resistance change over the life of the oil and the method includes heating the oil to a low temperature range and measuring a series of output voltages from the sensor. The present output voltage is compared to an immediately previous voltage value and based on this comparison, it is determined whether antifreeze is being dispersed in the engine oil. In this aspect, the low temperature range is from thirty degrees Celsius to forty degrees Celsius (30°–40°).

In another aspect of the present invention, the oil has a relatively slow resistance change over the life of the oil, and the method includes heating the oil to a predetermined middle temperature range and determining a threshold voltage value, Vth. A first difference value, $DV_1$, a second difference value, $DV_2$, and a third difference value, $DV_3$, are determined. These difference values, $DV_1$, $DV_2$, $DV_3$, are compared to the threshold voltage value, Vth. Based on the comparison, it is determined whether antifreeze is being dispersed in the engine oil. In this aspect, $V_{th}=A*Vref$, where A is a percentage value. Also, $V_{ref}=(V_{n-5}+V_{n-4}+V_{n-3})/3$, where $V_{ref}=$a starting reference voltage, $V_{n-5}=$a fifth previous voltage value, $V_{n-4}=$a fourth previous voltage value, $V_{n-3}=$a third previous voltage value. Moreover, $DV_1=abs(V_{n-2}-V_{ref})$, $DV_2=abs(V_{n-1}-V_{ref})$, and $DV_3=abs(V_n-V_{ref})$, where $V_{n-2}=$a second previous voltage value, $V_{n-1}=$a first previous voltage value, and $V_n=$a current voltage value. A is from ten percent to fifteen percent (10%–15%).

In this aspect of the present invention, the method also includes determining whether any two of the three difference values, $DV_1$, $DV_2$, $DV_3$, are greater than the threshold value, Vth. Based on this determination, it is indicated whether antifreeze is dispersed in the engine oil. In this aspect, the middle temperature range is from forty degrees Celsius to sixty degrees Celsius (40°–60°).

In yet another aspect of the present invention, an oil contamination sensor includes a first sensing electrode and a second sensing electrode. A sensing area is established between the electrodes and the sensing area is submerged in engine oil. This aspect of the present invention also includes a microprocessor connected to the sensing electrodes. The microprocessor includes a program for determining whether antifreeze is dispersed in the engine oil.

The present invention will now be described, by way of example, with reference to the accompanying drawings, in which:

DESCRIPTION OF AN EMBODIMENT OF THE INVENTION

Figure 1:
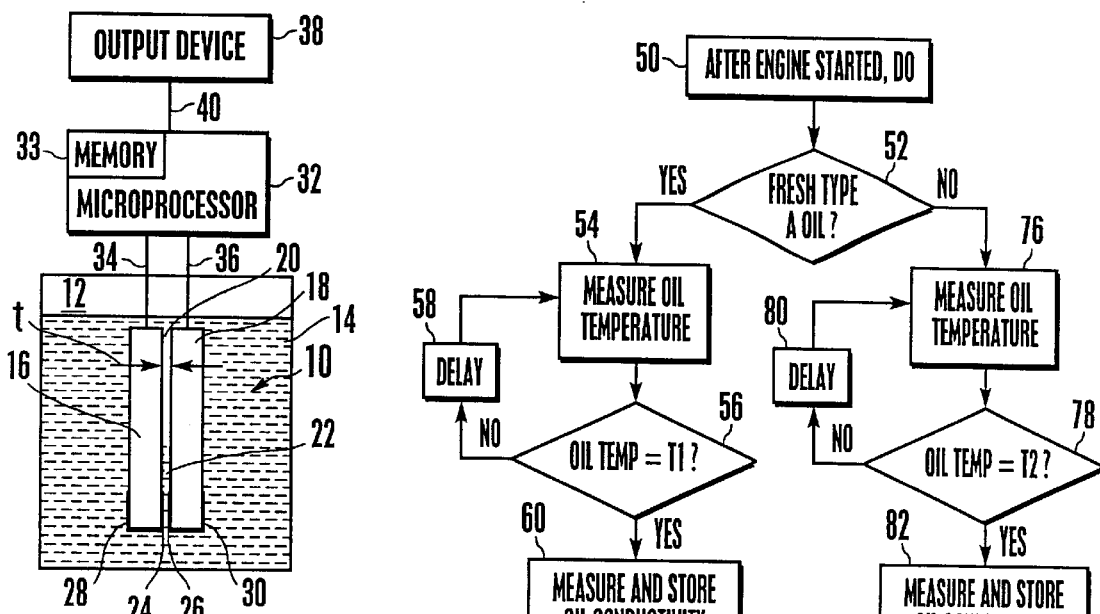
FIG. 1 is a plan view of an engine oil contamination sensor.

Referring initially to FIG. 1, an engine oil contamination sensor is shown and generally designated 10. FIG. 1 shows that the sensor 10 is installed in an oil pan 12 filled with oil 14. FIG. 1 shows that the sensor 10 includes an electrically insulative, preferably alumina, first plate 16 separated from an electrically insulative, preferably alumina, second plate 18 by a spacer 20. In a preferred embodiment, the spacer 20 is made of electrically insulative, rigid material, and is sandwiched between the plates 16, 18 in contact therewith.

As shown in FIG. 1, the plates 16, 18 are identical to each other in size and shape. The spacer 20, on the other hand, is shorter than the plates 16, 18 such that a sensing area 22 is formed between the plates 16, 18 below the spacer 20. In a preferred embodiment, the sensing area 22 is twenty millimeters (20 mm) deep and ten millimeters wide (10 mm), i.e., into the Figure as shown. Also, in a preferred embodiment, the spacer 20, has a thickness "t" of one millimeter (1 mm) such that the plates 16, 18 are spaced one millimeter (1 mm) apart.

As shown in FIG. 1, the first plate 16 and the second plate 18 respectively include a preferably platinum first sensing electrode 24 and a preferably platinum second sensing electrode 26. In a preferred embodiment, the electrodes 24, 26 are screen printed on the plates 16, 18. As shown, the electrodes 24, 26 flank the sensing area 22. FIG. 1 shows that the first plate 16 includes a first resistance temperature device (RTD) 28 on the side of the plate 16 opposite the first sensing electrode 24. Similarly, the second plate 18 includes a second RTD 30 opposite the second sensing electrode 26.

It is to be understood that an electrical line 34 connects the sensing electrodes 24, 26 to a microprocessor 32. On the other hand, an electrical line 36 connects the RTDs 28, 30 to the microprocessor 32. As shown, the microprocessor 32, in turn, is connected to an output device 38 by electrical line 40. Moreover, the microprocessor 32 includes a memory 33.

It is to be understood that the sensor 10 outputs a signal representing the resistance of the oil between the sensing electrodes 24, 26, i.e., within the sensing area 22. It is also to be understood that the microprocessor 32 can be, e.g., an engine control module (ECM), a body control module (BCM), or a powertrain control module (PCM) or other processor. In the case of a "smart" sensor the microprocessor 32 is within the sensor 10. Moreover, it is to be understood that the output device 38 can be an audible warning device, e.g., a buzzer or other audible alarm. The output device 38 can also be a visual warning device, e.g., a warning lamp or other visual display. Or, the output device 38 can be a visual indicator of the antifreeze content in the engine oil, e.g., a gauge or similar device. Also, more than one output device 38 can be used.

While the preferred implementation of the microprocessor 32 is an onboard chip such as a digital signal processor, it is to be understood that the logic disclosed below can be executed by other digital processors, such as by a personal computer. Or, the microprocessor 32 may be any computer, including a Unix computer, or OS/2 server, or Windows NT server, or a laptop computer.

The microprocessor 32 includes a series of computer-executable instructions, as described below, which will allow the microprocessor 32 to determine whether antifreeze is leaking into the engine oil. These instructions may reside, for example, in RAM of the microprocessor 32.

Alternatively, the instructions may be contained on a data storage device with a computer readable medium, such as a computer diskette. Or, the instructions may be stored on a magnetic tape, conventional hard disk drive, electronic read-only memory, optical storage device, or other appropriate data storage device. In an illustrative embodiment of the invention, the computer-executable instructions may be lines of compiled C++ compatible code.

The flow charts herein illustrate the structure of the logic of the present invention as embodied in computer program software. Those skilled in the art will appreciate that the flow charts illustrate the structures of computer program code elements including logic circuits on an integrated circuit, that function according to this invention. Manifestly, the invention is practiced in its essential embodiment by a machine component that renders the program elements in a form that instructs a digital processing apparatus (that is, a computer) to perform a sequence of function steps corresponding to those shown.

Figure 2:
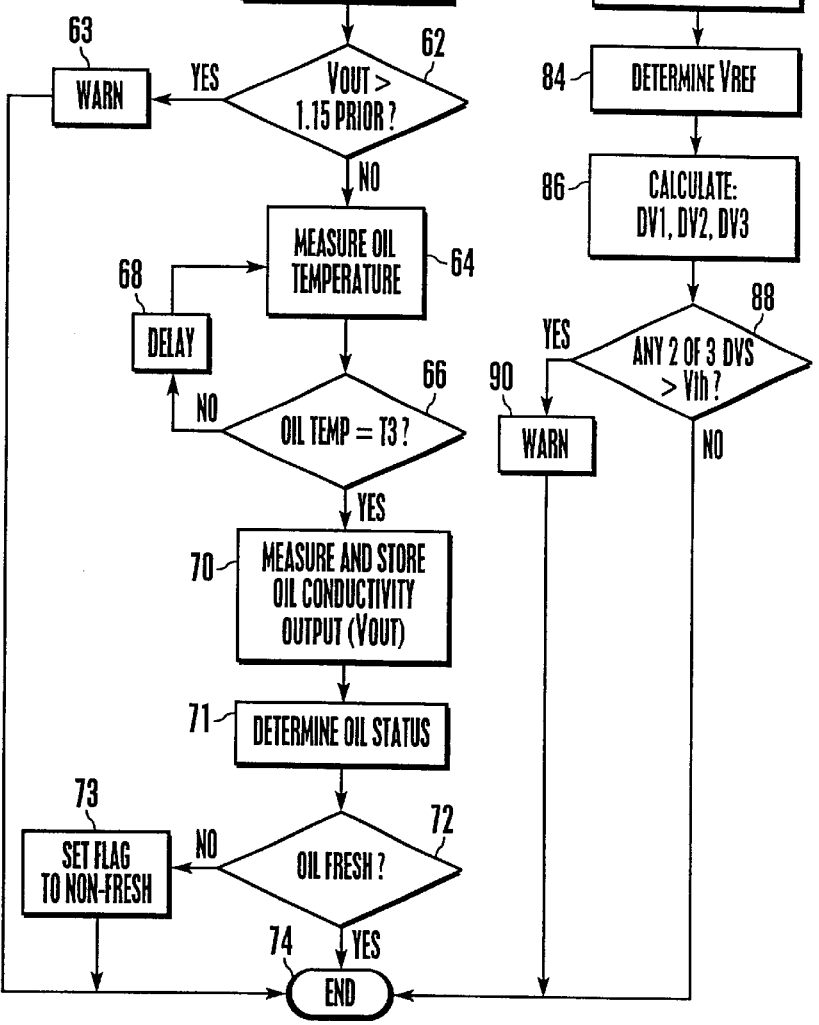
FIG. 2 is a flow chart of the operating logic of the present invention.

Referring now to FIG. 2, the operating logic of the present invention while the engine oil is heating up is shown. Commencing at block 50, after the engine is started, a do loop is entered wherein the succeeding steps are performed. At decision diamond 52, it is determined whether the oil 14 within the oil pan 12 is fresh type A oil or other, e.g., non-fresh type A oil, fresh type B oil, or non-fresh type B oil. Type A oils include oils that have rapid resistance changes as they age, e.g., during the first one thousand (1000) miles of vehicle operation. On the other hand, type B oils include those which have slow resistance changes as they age. The type of oil can be determined by measuring the resistance value of the fresh oil and comparing that value to known resistance values for fresh type A oils and fresh type B oils.

If at decision diamond 52, the oil 14 is fresh type A oil, the logic proceeds to block 54 where the oil temperature is measured. The logic then moves to decision diamond 56 where it is determined whether the oil temperature is within a predetermined range, T1, preferably from thirty degrees Celsius to forty degrees Celsius (30° C.–40° C.). If the oil temperature is not within the range, the logic moves to block 58 and delays for a predetermined time period before returning to block 54 to measure the oil temperature again. If the oil temperature is within the range, T1, the logic continues to block 60 wherein the oil conductivity output, $V_{out}$, of the sensor 10 is measured and stored. Then, at decision diamond 62, algorithm A is performed.

Algorithm A simply includes comparing the current output voltage of the sensor 10 to the previous output voltage of the sensor and determining whether the current sensor output voltage is fifteen percent (15%) greater than the previous output voltage. If so, the logic proceeds to block 63 where the microprocessor 32 sends a signal to an output device 38 in order to warn the driver that antifreeze is leaking into the engine oil 14. The logic then ends at state 74. On the other hand, if the current sensor output voltage is less than fifteen percent (15%) greater than the previous output voltage, the logic continues to block 64.

At block 64 the temperature of the oil 14 is again measured. Moving to decision diamond 66, it is determined whether the oil temperature is within a range, T3, preferably from seventy degrees Celsius to eighty degrees Celsius (70° C.–80° C.). If not, the logic proceeds to block 68 and delays for a predetermined time period before returning the block 64 to, again, measure the oil temperature. If the oil temperature is within the range, T3, the logic continues to block 70 where the oil conductivity output, $V_{out}$, of the sensor 10 is measured and stored. Then, at block 71, the type A oil status is determined, e.g., by checking the last N output values, e.g., the last ten (10) values. Moving to decision diamond 72, it is determined whether the oil is still fresh. For example, if the change from the Nth most recent value to the most recent value is less than ten percent (10%) of the Nth most recent value then the oil is no longer fresh and the flag in the memory 33 is set to "non-fresh" at block 73. The logic then ends at state 74.

Returning to decision diamond 52, if the oil is not fresh type A oil, the logic proceeds to block 76 where the oil temperature is measured. Then, at decision diamond 78 it is determined whether the oil temperature is within a range, T2, preferably from forty degrees Celsius to sixty degrees Celsius (40° C.–60° C.). If not, the logic moves to block 80 and delays for predetermined time period before returning to block 76 where the oil temperature is measured, again. If the temperature is within the range, T2, the logic moves to block 82 where the oil conductivity output, $V_{out}$, of the sensor 10 is measured and stored. Then, starting at block 84 algorithm B is performed. At block 84, a reference voltage is determined as follows:

$$V_{ref}=(V_{n-5}+V_{n-4}+V_{n-3})/3$$

where, $V_{ref}$=starting reference voltage of the sensor 10

$V_{n-5}$=the fifth previous voltage value of the sensor 10

$V_{n-4}$=the fourth previous voltage value of the sensor 10

$V_{n-3}$=the third previous voltage value of the sensor 10

Then, at block 86, three difference values, each of which is equal to the absolute value of the difference between two voltages, are calculated as follows:

$$DV_1 = abs\ (V_{n-2} - V_{ref})$$

$$DV_2 = abs\ (V_{n-1} - V_{ref})$$

$$DV_3 = abs\ (V_n - V_{ref})$$

where, $V_{n-2}$=the second previous voltage value $V_{n-1}$=the first previous voltage value $V_n$=the current voltage value Proceeding to decision diamond 88, it is determined whether any two of the three difference values are greater than a threshold value, Vth. Vth is equal to $A*V_{ref}$ where A is preferably from ten percent to fifteen percent (10%–15%). If any two of the three difference values are greater than Vth, the logic moves to block 90 where the microprocessor 32 sends a signal to the output device 38 to indicate that antifreeze is leaking into the engine oil 14 and thus, to warn the driver. The logic then ends at state 74. If not, the logic also ends at state 74.

It is to be understood that for oil other than fresh type A oil, there is a turning point where the resistance of the oil switches from positive to negative. Thus, if the leakage of antifreeze is in very small increments, then the leakage can be detected before the turning point. Any interference caused by the addition of oil to the oil pan, e.g., greater than one-half quart, the sensor will detect the addition of the oil and reset the initial value.

Figure 3:
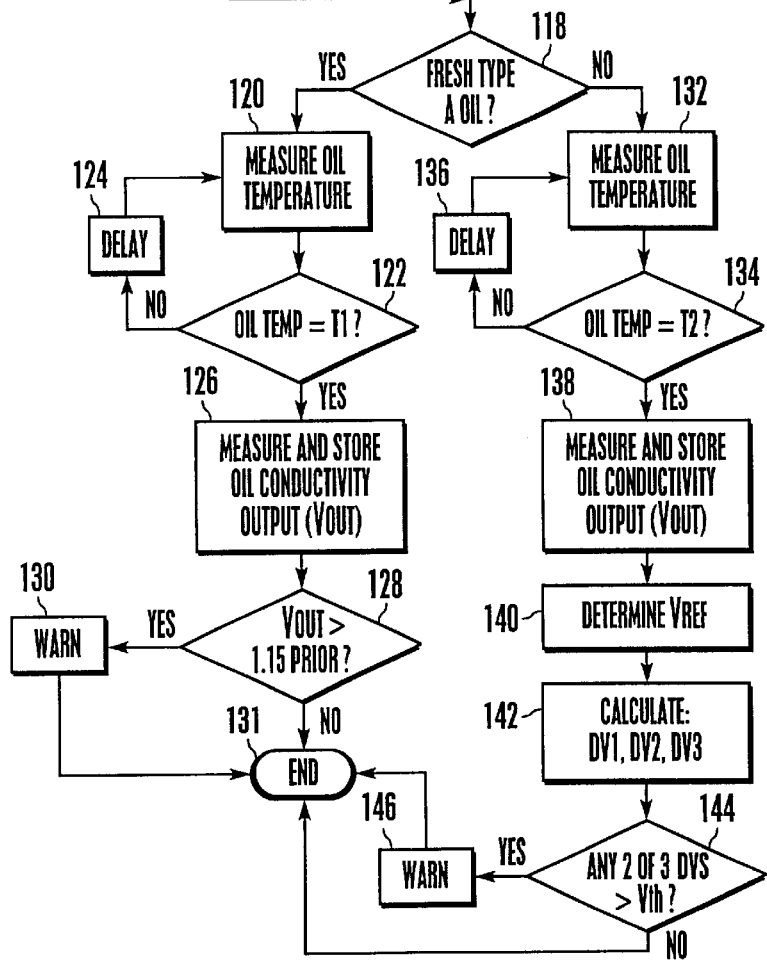
FIG. 3 is a flow chart of the operating logic

Referring now to FIG. 3, the operating logic of the present invention while the engine oil is cooling off is shown. Commencing at block 100, after the engine is stopped, a do loop is entered wherein the succeeding steps are performed. At block 102 the temperature of the oil 14 is measured. Moving to decision diamond 104, it is determined whether the oil temperature is within a range, T3, preferably from seventy degrees Celsius to eighty degrees Celsius (70° C.–80° C.). If not, the logic proceeds to block 106 and delays for a predetermined time period before returning the block 102 to, again, measure the oil temperature. If the oil temperature is within the range, T3, the logic continues to block 108 where the oil conductivity output, $V_{out}$, of the sensor 10 is measured and stored. Then, at block 110, the oil status is determined, e.g., by checking the last N output values of the sensor 10, e.g., the last ten (10) values. Moving to decision diamond 112, it is determined whether the oil is still fresh. For example, if the change from the Nth most recent value to the most recent value is less than ten percent (10%) of the Nth most recent value then the oil is no longer fresh and the flag in the memory 33 is set to "non-fresh" at block 114. On the other hand, the flag in the memory 33 is set to "fresh" at block 116.

Regardless, once the memory flag is set to "fresh" or "non-fresh", the logic moves to decision diamond 118 where it is determined whether the oil 14 within the oil pan 12 is fresh type A oil or other, e.g., non-fresh type A, fresh type B oil or non-fresh type B oil. If at decision diamond 118, the oil 14 is fresh type A oil, the logic proceeds to block 120 where the oil temperature is measured. The logic then moves to decision diamond 122 where it is determined whether the oil temperature is within a predetermined range, T1, preferably from thirty degrees Celsius to forty degrees Celsius (30° C.-40° C.). If the oil temperature is not within the range, T1, the logic moves to block 124 and delays for a predetermined time period before returning to block 120 to measure the oil temperature again. If the oil temperature is within the range, T1, the logic continues to block 126 wherein the oil conductivity output, $V_{out}$, of the sensor 10 is measured and stored. Then, at decision diamond 128, algorithm A is performed.

Algorithm A simply includes comparing the current output voltage of the sensor 10 to the previous output voltage of the sensor and determining whether the current sensor output voltage is fifteen percent (15%) greater than the previous output voltage. If so, the logic proceeds to block 130 where the microprocessor 32 sends a signal to an output device 38 in order to warn the driver that antifreeze is leaking into the engine oil 14 and ends at state 130. If not, the logic moves to state 131 and ends.

Returning to decision diamond 118, if the oil is not fresh type A oil, the logic proceeds to block 132 where the oil temperature is measured. Then, at decision diamond 134 it is determined whether the oil temperature is within a range, T2, preferably from forty degrees Celsius to sixty degrees Celsius (40° C.–60° C). If not, the logic moves to block 136 and delays for predetermined time period before returning to block 132 where the oil temperature is measured, again. If the temperature is within the range, T2, the logic moves to block 138 where the oil conductivity output, $V_{out}$, of the sensor 10 is measured and stored. Then, starting at block 140 algorithm B is performed. At block 140, a reference voltage is determined as follows:

$$V_{ref} = (V_{n-5} + V_{n-4} + V_{n-3})/3$$

where, $V_{ref}$=starting reference voltage of the sensor 10

$V_{n-5}$=the fifth previous voltage value of the sensor 10

$V_{n-4}$=the fourth previous voltage value of the sensor 10

$V_{n-3}$=the third previous voltage value of the sensor 10

Then, at block 142, three difference values, each of which is equal to the absolute value of the difference between two voltages, are calculated as follows:

$$DV_1 = abs\ (V_{n-2} - V_{ref})$$

$$DV_2 = abs\ (V_{n-1} - V_{ref})$$

$$DV_3 = abs\ (V_n - V_{ref})$$

where, $V_{n-2}$=the second previous voltage value $V_{n-1}$=the first previous voltage value $V_n$=the current voltage value Proceeding to decision diamond 144, it is determined whether any two of the three difference values are greater than a threshold value, Vth. Vth is equal to $A*V_{ref}$ where A is preferably from ten percent to fifteen percent (10%–15%). If any two of the three difference values are greater than Vth, the logic moves to block 146 where the microprocessor 32 sends a signal to the output device 38 to indicate that antifreeze is leaking into the engine oil 14 and thus, to warn the driver. The logic then ends at state 131. If not, the logic also ends at state 131.

Figure 4:
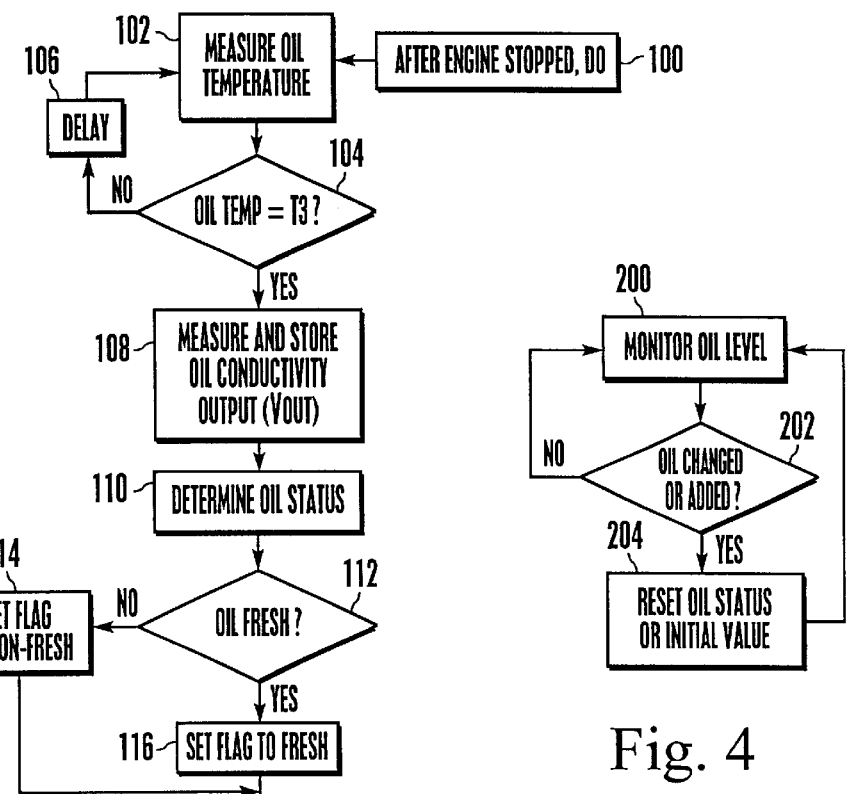
FIG. 4 is a flow chart of the reset logic.

Referring to FIG. 4, the reset logic is shown and commences at block 200 where the oil level is monitored. It is to be understood that the oil condition sensor 10, described above, can be incorporated into an oil level sensor to create an oil condition/level sensor (OCLS). Moving to decision diamond 202, it is determined whether a predetermined quantity of oil, e.g., greater than one-half quart, has been added to the oil pan 12 or whether the oil in the oil pan 12 has been changed. If so, the logic moves to block 204 where the oil status or initial voltage value of the sensor 10 is reset. If not, the logic returns to block 200 and the oil level continues to be monitored.

It is to be understood that the effects of water on the resistance of the engine oil are similar to antifreeze. Normally, the antifreeze is mixed with water in the coolant system at a one-to-one ratio. Therefore, water leaks into the engine oil 14 with the antifreeze. The amount of antifreeze and water existing in the engine oil can be estimated separately by conducting the sensor 10 measurement twice within the predetermined temperature ranges, e.g., once while the oil 14 is heating up and then again while the oil is cooling down. Under normal conditions, the operating temperature of the engine oil 14 is in a range from eighty degrees Celsius and one hundred twenty degrees Celsius (80° C.–120° C.). As soon as the oil temperature exceeds eighty degrees Celsius (80° C.), the water evaporates quickly. Therefore, the sensor outputs measured while the oil is cooling down can be used to estimate the amount of antifreeze in the oil only. In addition, the difference between the measurement taken while the oil is heating up and the measurement taken while the oil is cooling down can be correlated to the amount of water existing in the oil prior to vehicle operation.

During short trips and cold start services, the oil temperature would never exceed eight degrees Celsius (80° C.) and relatively large amounts of water can be condensed in the engine oil. Water condensation in the engine oil can also be detected using the above logic. Furthermore, if the oil temperature does not exceed eighty degrees Celsius (80° C.) for more than five consecutive times of vehicle operation, then it is a strong likelihood that the contamination in the oil 14 is water. Instead of warning the driver to change the oil, the driver can be instructed to drive the vehicle on a highway for a relatively long distance, e.g., more than sixty miles. By doing so, the water would be evaporated, and the lubricating and protecting functions of engine oil would be restored.

With the configuration of structure described above, it is to be appreciated that the engine oil contamination sensor provides a means for indicating to the driver when the engine oil is contaminated with antifreeze before the build-up of harmful undispersed antifreeze. Thus, the problem can be fixed long before catastrophic harm befalls the engine components. Moreover, each embodiment of the logic shown above utilizes two algorithms, e.g., one for fresh type A oil and one for all other oils (non-fresh type A oil, fresh type B oil, and non-fresh type B oil.) A flag in the memory 33 of the microprocessor is used to record the status of the oil, i.e., fresh or non-fresh. After an oil change, the flag is set as fresh. Conversely, after a certain mileage, e.g., one thousand miles (1000 miles), the sensor may detect that the oil is no longer fresh and set the flag to non-fresh.

While the particular ENGINE OIL CONTAMINATION SENSOR as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

What is claimed is:

1. A method for determining dispersed antifreeze contamination of oil within an engine using an oil contamination sensor, wherein the oil has a relatively slow resistance change over the life of the oil, comprising the acts of:

allowing the oil to pass through a temperature gradient;

measuring the output voltage of the sensor;

at least partially based on the output voltage of the sensor, determining whether antifreeze is being dispersed in the oil determining when the oil temperature is within a middle temperature range;

determining a threshold voltage value, Vth;

determining a first difference value, $DV_1$;

determining a second difference value, $DV_2$;

determining a third difference value, $DV_3$;

comparing the difference values, $DV_1$, $DV_2$, $DV_3$, to the threshold voltage value, Vth; and at least partially based on the comparing act, determining whether antifreeze is being dispersed in the engine oil.

2. The method of claim 1, where:

$V_{th}$=A*Vref, where A is a percentage value and $V_{ref}=(V_{n-5}+V_{n-4}+V_{n-3})/3$, where $V_{ref}$=a starting reference voltage, $V_{n-5}$=a fifth previous voltage value, $V_{n-4}$=a fourth previous voltage value, $V_{n-3}$=a third previous voltage value; and $DV_1$=abs $(V_{n-2}-V_{ref})$, $DV_2$=abs $(V_{n-1}-V_{ref})$, $DV_3$=abs $(V_n-V_{ref})$, where $V_{n-2}$=a second previous voltage value, $V_{n-1}$=a first previous voltage value, and $V_n$=a current voltage value.

3. The method of claim 2, where A is from ten percent to fifteen percent (10%–15%).

4. The method of claim 3, further comprising the acts of:

determining whether any two of the three difference values, $DV_1$, $DV_2$, $DV_3$, are greater than the threshold value, Vth; and at least partially based on the determining act, indicating whether antifreeze is dispersed in the engine oil.

5. The method of claim 1, wherein the middle temperature range is from forty degrees Celsius to sixty degrees Celsius (40°–60°).

6. The method of claim 1, where the oil has a relatively rapid resistance change over the life of the oil, and the method further comprises the acts of:

measuring a series of output voltages from the sensor at a low temperature range;

comparing a present output voltage to an immediately previous voltage value; and at least partially based on the comparing act, determining whether antifreeze is being dispersed in the engine oil.

7. The method of claim 6, wherein the low temperature range is from thirty degrees Celsius to forty degrees Celsius (30° C.-40° C.).

8. An oil contamination sensor, comprising:

a first sensing electrode;

a second sensing electrode;

a sensing area established between the electrodes, the sensing area being submerged in an engine oil having a relatively slow resistance change over the life of the oil;

a microprocessor connected to the sensing electrodes, the microprocessor including a program for determining whether antifreeze is dispersed in the engine oil, the program comprising:

logic means for measuring the output voltage of the sensor, while the engine oil is passing through a temperature gradient;

logic means for determining whether antifreeze is being dispersed in the oil at least partially based on the output voltage of the sensor;

logic means for determining when the oil temperature is within a predetermined middle temperature range;

logic means for determining a threshold voltage value, Vth;

logic means for determining a first difference value, $DV_1$;

logic means for determining a second difference value, $DV_2$;

logic means for determining a third difference value, $DV_3$;

logic means for comparing the difference values, $DV_1$, $DV_2$, $DV_3$, to the threshold voltage value, Vth; and logic means for determining whether antifreeze is being dispersed in the engine oil at least partially based on the comparing act.

9. The sensor of claim 8, where:

$V_{th}=A*V_{ref}$, where A is a percentage value and $V_{ref}=(V_{n-5}+V_{n-4}+V_{n-3})/3$, where $V_{ref}$=a starting reference voltage, $V_{n-5}$=a fifth previous voltage value, $V_{n-4}$=a fourth previous voltage value, $V_{n-3}$=a third previous voltage value; and $DV_1$=abs $(V_{n-2}-V_{ref})$, $DV_2$=abs $(V_{n-1}-V_{ref})$, $DV_3$ =abs $(V_n-V_{ref})$, where $V_{n-2}$=a second previous voltage value, $V_{n-1}$=a first previous voltage value, and $V_n$=a current voltage value.

10. The sensor of claim 9, where A is from ten percent to fifteen percent (10%–15%).

11. The sensor of claim 10, wherein the program further comprises:

logic means for determining whether any two of the three difference values, $DV_1$, $DV_2$, $DV_3$, are greater than the threshold value, Vth; and logic means for indicating that antifreeze is dispersed in the engine oil at least partially based on the determining act.

12. The sensor of claim 8, wherein the middle temperature range is from forty degrees Celsius to sixty degrees Celsius (40°–60°).

13. The sensor of claim 8, further comprising:

an output device connected to the microprocessor, the output device receiving a signal from the microprocessor when antifreeze is being dispersed in engine oil.

14. The sensor of claim 8, further comprising:

a spacer disposed between the electrodes.

15. The sensor of claim 8, wherein the sensor is placed in an oil having a relatively rapid resistance change over the life of the oil, and the program further comprises:

logic means for measuring a series of output voltages from the sensor, while the oil is in a low temperature range;

logic means for comparing a present output voltage to an immediately previous voltage value; and logic means for determining whether antifreeze is being dispersed in the engine oil at least partially based on the comparing act.

16. The sensor of claim 15, wherein the low temperature range is from thirty degrees Celsius to forty degrees Celsius (30° C.-40° C.).

* * * * *